United States Patent
Moulton et al.

(10) Patent No.: US 6,953,448 B2
(45) Date of Patent: *Oct. 11, 2005

(54) CANTILEVER PUSH TAB FOR AN INTRAVENOUS MEDICAL DEVICE

(75) Inventors: William G. Moulton, West Jordan, UT (US); Christopher N. Cindrich, South Jordan, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 27 days.

This patent is subject to a terminal disclaimer.

(21) Appl. No.: 10/667,092

(22) Filed: Sep. 18, 2003

(65) Prior Publication Data

US 2004/0102735 A1 May 27, 2004

Related U.S. Application Data

(63) Continuation of application No. 09/865,915, filed on May 25, 2001, now Pat. No. 6,638,252.

(51) Int. Cl.[7] .................. A61M 5/178; A61M 25/16; A61M 25/18; A61M 39/00; A61M 39/10
(52) U.S. Cl. .................. 604/164.01; 604/533
(58) Field of Search .................. 604/162, 164.01, 604/164.07, 164.08, 164.09, 165.01, 171, 187, 192, 198, 263, 264, 272, 533

(56) References Cited

U.S. PATENT DOCUMENTS

| | | | | |
|---|---|---|---|---|
| 4,193,400 A | * | 3/1980 | Loveless et al. | 604/168.01 |
| 4,326,519 A | * | 4/1982 | D'Alo et al. | 604/165.04 |
| 4,863,432 A | * | 9/1989 | Kvalo | 604/177 |
| 4,964,854 A | * | 10/1990 | Luther | 604/166.01 |
| 5,098,405 A | * | 3/1992 | Peterson et al. | 604/247 |
| 5,215,528 A | * | 6/1993 | Purdy et al. | 604/164.08 |
| 5,370,624 A | * | 12/1994 | Edwards et al. | 604/167.05 |
| 5,685,855 A | * | 11/1997 | Erskine | 604/168.01 |
| 5,688,249 A | * | 11/1997 | Chang et al. | 604/198 |
| 5,713,876 A | * | 2/1998 | Bogert et al. | 604/243 |
| 5,795,339 A | * | 8/1998 | Erskine | 604/264 |
| 5,911,705 A | * | 6/1999 | Howell | 604/110 |
| 5,951,525 A | * | 9/1999 | Thorne et al. | 604/198 |
| 5,957,893 A | * | 9/1999 | Luther et al. | 604/164.01 |
| 5,971,958 A | * | 10/1999 | Zhang | 604/165.02 |
| 5,976,115 A | * | 11/1999 | Parris et al. | 604/533 |
| 6,004,294 A | * | 12/1999 | Brimhall et al. | 604/164.08 |
| 6,050,976 A | * | 4/2000 | Thorne et al. | 604/164.01 |
| 6,171,281 B1 | * | 1/2001 | Zhang | 604/164.01 |
| 6,638,252 B2 | * | 10/2003 | Moulton et al. | 604/164.01 |

* cited by examiner

Primary Examiner—Nicholas D. Lucchesi
Assistant Examiner—Mark K. Han
(74) Attorney, Agent, or Firm—Mony R. Ghose

(57) ABSTRACT

A combination cantilever push tab and finger rest is associated with the needle shield and extends distally from the distal end of the needle shield. The cantilever push tab and finger rest includes a cantilever portion that extends distally from the needle shield, preferably from an exterior surface of the needle shield, and an upstanding tab portion at the distal end of the cantilever portion. This configuration causes the upstanding tab to extend over the proximal portion of the catheter adapter and allows a clinician to insert a catheter using virtually any clinically acceptable technique for inserting a catheter into a patient.

17 Claims, 7 Drawing Sheets

CANTILEVER PUSH TAB FOR AN INTRAVENOUS MEDICAL DEVICE

This application is a continuation of application Ser. No. 09/865,915, filed May 25, 2001, now U.S. Pat. No. 6,638,252.

BACKGROUND OF THE INVENTION

The subject invention relates to a cantilever push tab for a medical device. More specifically, the cantilever push tab is especially adapted for use with introducer needle assemblies that may be used in conjunction with intravenous catheters, as well as catheter introducers and guidewire introducers.

In order properly to place medical devices such as intravenous ("IV") catheters into a patient, the catheter is typically mounted over an introducer needle having a sharp distal tip. At least the distal portion of the catheter tightly engages the outer surface of the needle to prevent peelback of the catheter and thus facilitates insertion of the catheter into the blood vessel. The distal tip of the needle preferably extends beyond the distal tip of the catheter with the bevel of the needle facing up away from the patient's skin.

The catheter and introducer needle assembly is inserted at a shallow angle through the patient's skin into a blood vessel. In typical assemblies, the clinician confirms that there is flashback of blood in a flashback chamber associated with the needle assembly in order to verify proper placement of the catheter in the blood vessel. The flashback chamber is typically formed as part of the needle hub. Once proper placement of the catheter into the blood vessel is confirmed, the clinician applies pressure to the blood vessel by pressing down on the patient's skin over the blood vessel distal of the needle and the catheter. This finger pressure occludes or at least minimizes further blood flow through the needle and the catheter. The clinician then withdraws the needle, leaving the catheter in place for use in accordance with standard medical technique.

Clinicians may use various techniques for inserting a catheter into a patient. This variety of techniques also comes into play because there are different types of catheters, such as straight and ported catheters, that may be used. A ported catheter includes a radially extending side port integral with the catheter adapter. See for example the catheter disclosed in U.S. Pat. No. 5,098,405. In a ported catheter, the fluid-handling device normally connected to the catheter is connected to the proximal end of the catheter adapter with the side port providing access to the catheter and thus the patient's vasculature for intermittent injections of medicaments. Such ported catheters are typically used in Europe. With a ported catheter, the clinician typically grasps the assembly by placing the thumb of one hand on the proximal end of the needle hub and the forefinger or middle finger of that same hand on the side port of the catheter adapter and, where there is a wing, the other finger is placed on the wing. A straight catheter does not include a side port so that the fluid-handling device is connected to the proximal end of the catheter adapter. See for example the catheters disclosed in U.S. Pat. No. 4,193,400 and U.S. Pat. No. 5,685,855. Such straight catheters are typically used in the United States. With a straight catheter, the clinician typically grasps the assembly by placing the thumb and forefinger or middle finger of one hand on either side of the needle hub. If the middle finger is used, the forefinger of that hand can be used to push against a push tab that may be formed on the top of the catheter adapter to facilitate the advancement of the catheter off of the needle. Alternatively, the other hand can be used to push against the push tab.

Once a clinician learns a particular technique to insert a particular type of catheter into a patient, that clinician will typically continue to use that insertion technique and the catheter associated with that technique, for inserting the catheter into a patient. The technique sensitive nature of catheter insertion procedures is exacerbated by the structural differences between ported catheters and straight catheters. Thus, a clinician trained to insert a ported catheter may have difficulty adjusting to inserting a straight catheter. Similarly, a clinician trained to insert a straight catheter may have difficulty adjusting to inserting a ported catheter.

This requires medical device manufacturers to produce and maintain an adequate supply of both ported and straight catheters in order to meet the needs of clinicians. This is costly and potentially wasteful for the manufacturer.

SUMMARY OF THE INVENTION

It is therefore an object of this invention to provide an introducer needle assembly for a medical device, such as an IV catheter, to allow clinicians to use virtually any clinically acceptable technique for inserting the catheter.

It is another object of this invention to provide an introducer needle assembly for a medical device, such as an IV catheter, to allow clinicians to insert a catheter into a patient without regard to whether that clinician has been trained to use ported catheters or straight catheters.

The IV catheter typically used with the introducer needle assembly of this invention is coaxially disposed over the introducer needle with the distal portion of the catheter tightly engaging the outer surface of the introducer needle. This prevents peelback of the catheter and facilitates insertion of the catheter into the patient's blood vessel. Prior to use, the catheter is located about the introducer needle so that the sharp distal tip of the introducer needle is distal of the distal end of the catheter. The proximal end of the catheter is connected to a catheter adapter.

The introducer needle has a sharp distal tip and a proximal end connected to the distal end of a needle hub. A flashback chamber may be defined in the needle hub. Where such a flashback chamber is used, a vented plug is located in the open proximal end of the flashback chamber to allow air to escape from the flashback chamber when blood enters the flashback chamber from the introducer needle. Alternatively, the introducer needle could define a notch, i.e. an opening in the sidewall of the introducer needle, and an integrated extension tube could extend from the catheter adapter. In this embodiment, flashback of blood can be observed in the catheter and the integrated extension tube as blood flows through the notch into the annular space between the needle and the catheter and into the extension tube once a successful venipuncture has been made.

A needle shield is movably disposed about the introducer needle and located distally of the needle hub. The needle shield is defined by a housing having an internal cavity through which the introducer needle extends. A lock associated with the needle shield prevents unwanted distal movement of the introducer needle once the introducer needle has been proximally withdrawn into the needle shield. Also associated with the needle shield is a means for preventing unwanted proximal movement of the introducer needle once the sharp distal tip of the introducer needle has been proximally withdrawn into the needle shield.

A cantilever push tab is associated with the needle shield and extends distally from the distal end of the needle shield.

As its name implies, the cantilever push tab includes a cantilever portion that extends distally from the needle shield, preferably from an exterior surface of the needle shield, and an upstanding tab portion adjacent to the distal end of the cantilever portion. This configuration causes the upstanding tab to extend over the proximal portion of the catheter adapter and allows a clinician to insert a catheter into a patient using virtually any clinically acceptable technique. For example, the clinician can use a single-handed technique that is typically used for inserting a ported catheter. In addition, a clinician can initially disregard the cantilever push tab and insert a catheter using a single-handed technique typically used for inserting a straight catheter and use the cantilever push tab to advance the catheter off of the introducer needle. Alternatively, a clinician can use a two-handed technique and push against the cantilever push tab with her other hand to insert the catheter into a patient. As can be seen from the foregoing discussion, the cantilever push tab provides maximum flexibility and allows a clinician to insert a catheter used in conjunction with an introducer needle assembly of this invention with virtually any clinically acceptable technique.

BRIEF DESCRIPTION OF THE DRAWINGS

The preferred embodiments are illustrated in the drawings in which like reference numerals refer to like elements and in which.

DETAILED DESCRIPTION OF THE INVENTION

Figure 1:
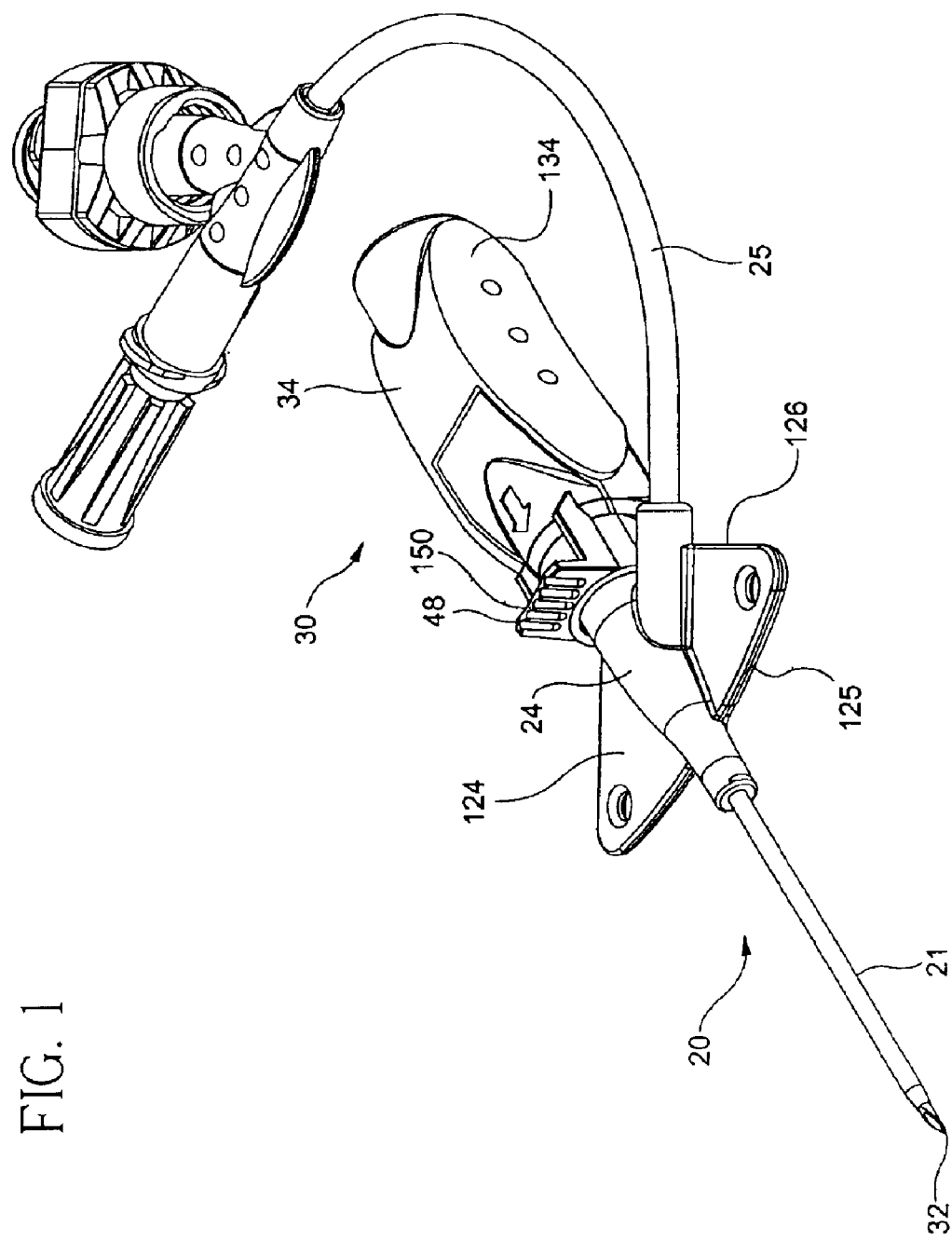
FIG. 1 is a perspective view of an integrated catheter with an introducer needle assembly including the cantilever push tab of this invention ready for use.
Figure 2:
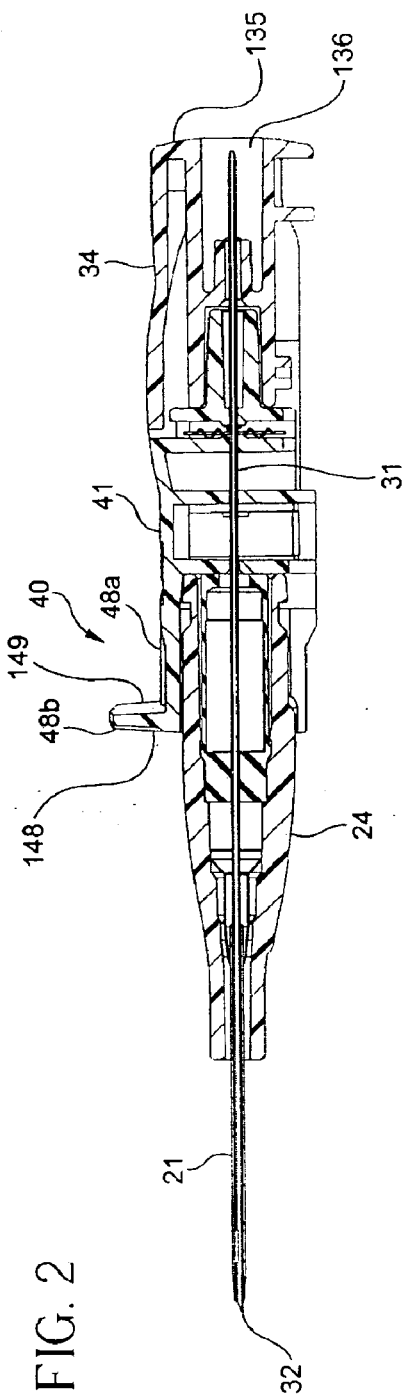
FIG. 2 is a side elevation view in cross section of a catheter with an introducer needle assembly including the cantilever push tab of this invention ready for use.
Figure 3:
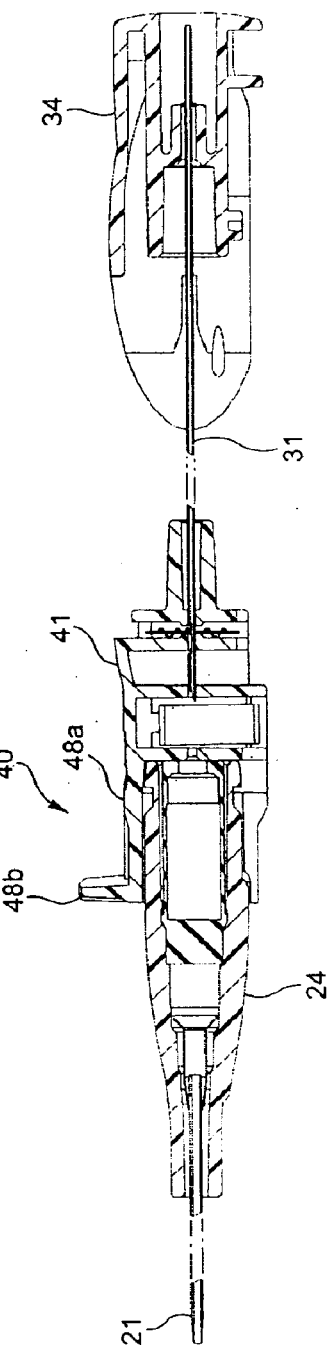
FIG. 3 is a side elevation view in cross section of a catheter with an introducer needle assembly including the cantilever push tab of this invention with the catheter and needle shield advanced distally with respect to the needle hub.
Figure 4:
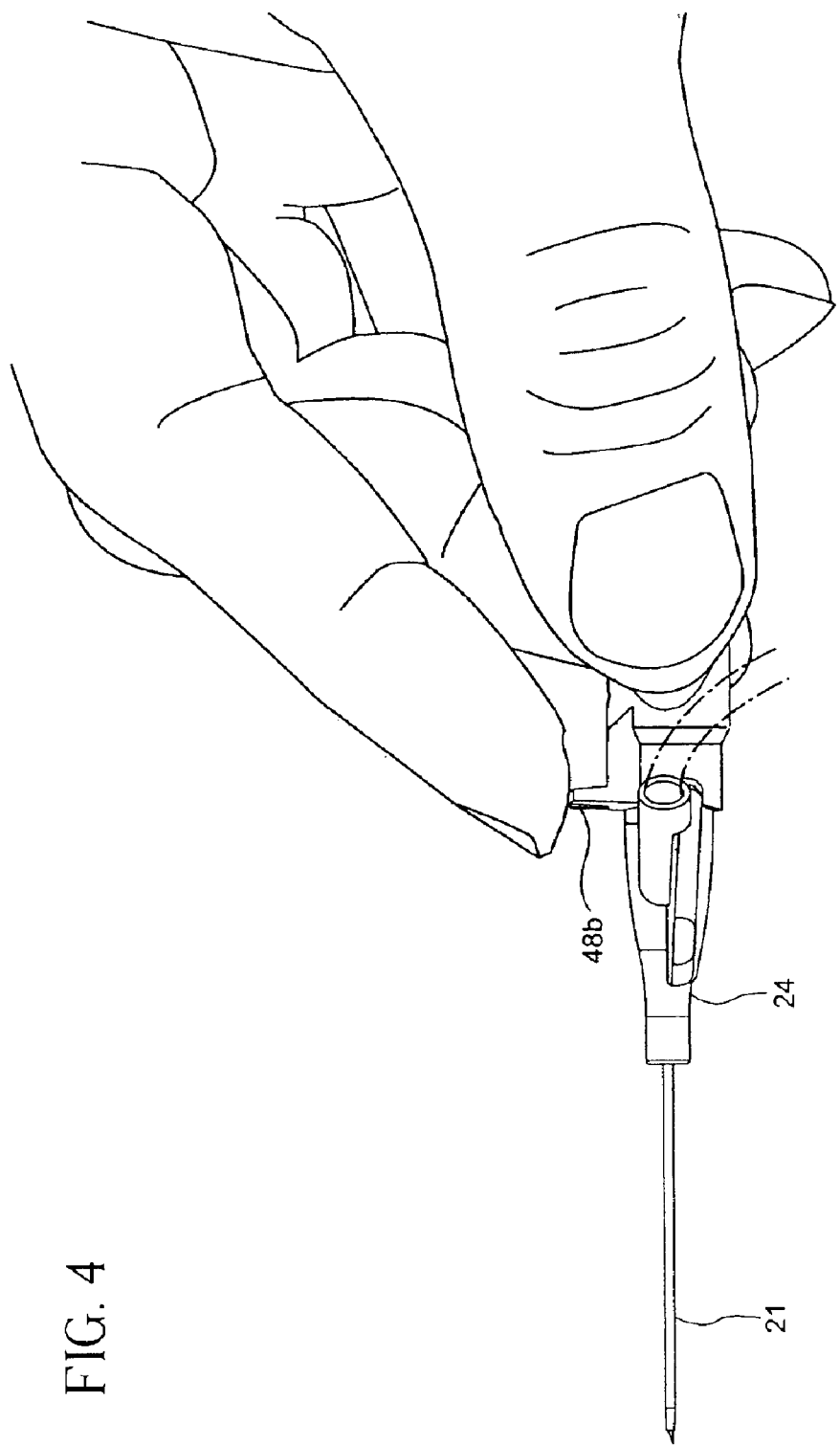
FIG. 4 is a side elevation view of a catheter with an introducer needle assembly including the cantilever push tab of this invention ready for use and the clinician's fingers in the position used for inserting straight catheters with a single hand.
Figure 5:
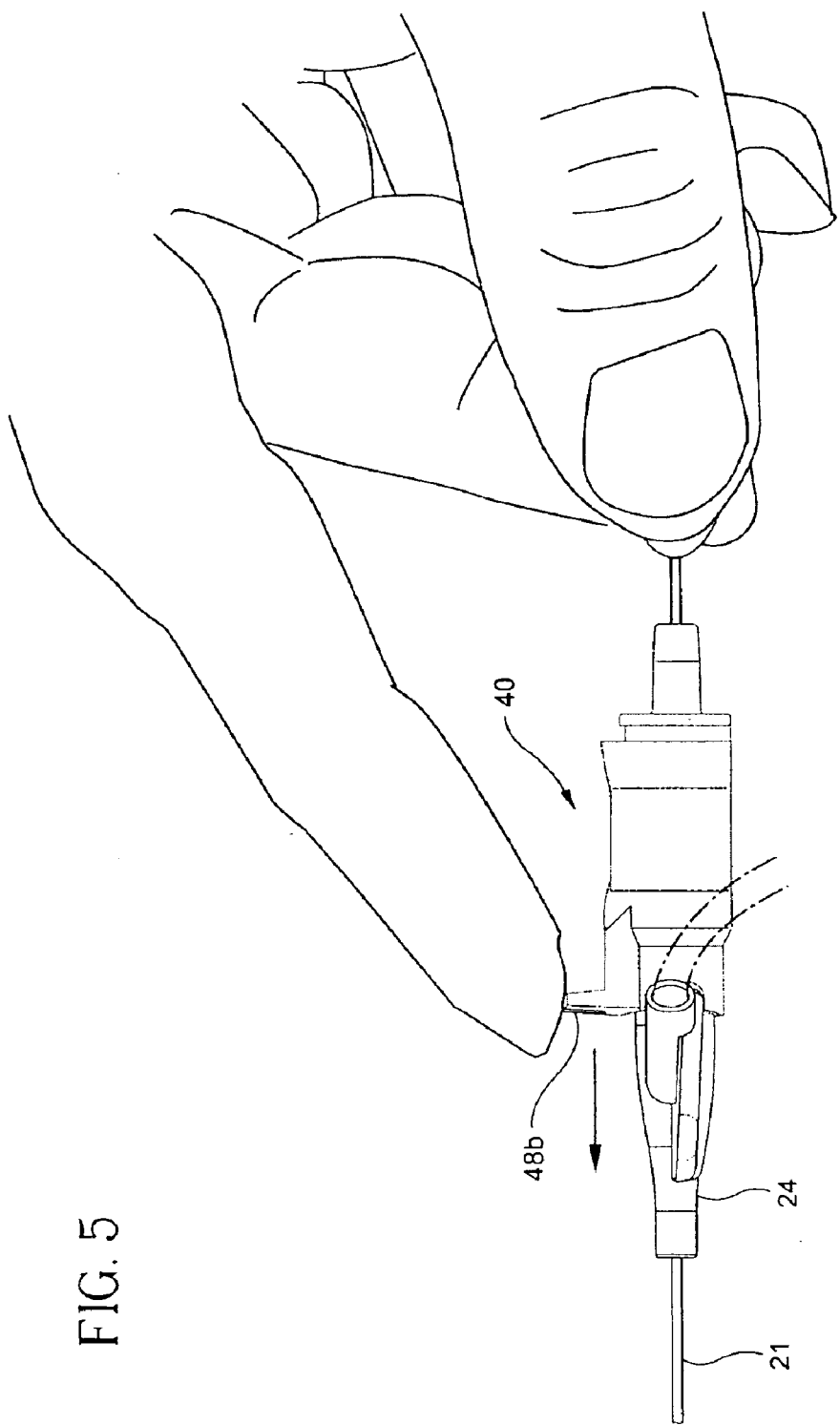
FIG. 5 is a side elevation view of a catheter with an introducer needle assembly including the cantilever push tab of this invention and the clinician's fingers in the position typically used for inserting straight catheters where the catheter and needle shield have been advanced distally with respect to the needle hub.
Figure 6:
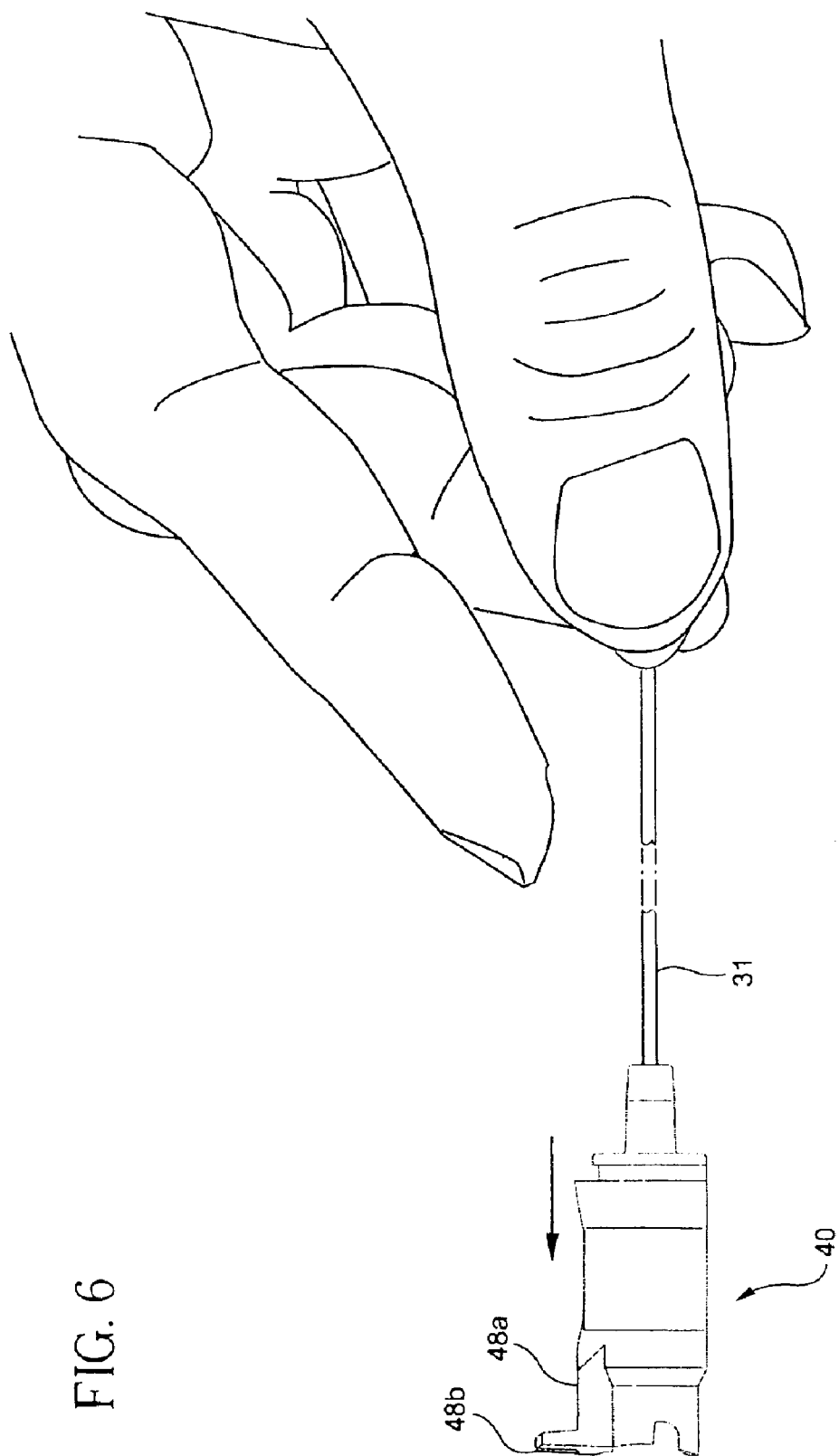
FIG. 6 is a side elevation view of an introducer needle assembly including the cantilever push tab of this invention and the clinician's fingers indicated in the position typically used for inserting straight catheters where the needle shield has been moved distally over the sharp distal tip of the needle after the catheter has been located in the patient.

As used herein, the term "proximal" refers to a location with respect to the device during normal use that is closest to the clinician and farthest from the patient. Conversely, the term "distal" refers to a location with respect to the device during normal use that is farthest from the clinician and closest to the patient. As used herein, the term "top", "up" or "upwardly" refers to a location with respect to the device during normal use that is radially away from the longitudinal axis of the device and away from the patient's skin. Conversely, as used herein, the term "bottom", "down" or "downwardly" refers to a location with respect to the device during normal use that is radially away from the longitudinal axis of the device and toward the patient's skin. As used herein, the term "in" or "inwardly" refers to a location with respect to the device during normal use that is toward the inside of the device. Conversely, as used herein, the term "out" or "outwardly" refers to a location with respect to the device during normal use that is toward the outside of the device.

This invention is described herein using like reference numbers for like elements in the different embodiments. It is to be understood that this invention is applicable to catheters having an integrated extension tube ("integrated catheters") as well as other catheters such as standard peripheral IV catheters. In addition, it is to be understood that this invention is applicable to catheter introducers and guidewire introducers and other medical devices that are designed to be inserted into a patient's vasculature using a standard over the needle insertion technique. Finally, while this invention is satisfied by embodiments in many different forms, there are shown in the drawings and herein described in detail, preferred embodiments of the invention with the scope of the invention measured by the appended claims.

The introducer needle assembly including the cantilever push tab of this invention is preferably used to insert an integrated catheter assembly 20 into a patient. Catheter assembly 20 includes a catheter 21 that has a proximal end, a distal end and a catheter adapter 24 affixed to the proximal end of catheter 21. Suitable materials for catheter 21 include, but are not limited to, thermoplastic resins such as fluorinated ethylene propylene (FEP), polytetrafluoroethylene (PTFE), polyurethane and the like. Preferably, catheter 21 is formed from a thermoplastic hydrophilic polyurethane that softens with exposure to physiological conditions present in the patient's body. Suitable materials for catheter adapter 24 include, but are not limited to, thermoplastic polymeric resins such as polycarbonate, polystyrene, polypropylene and the like. An integrated extension tube 25 extends from catheter adapter 24 and may include a fluid flow control device at its proximal end. See FIG. 1. Details of such an integrated catheter are described generally in U.S. Pat. No. 5,697,914. Wings 124 are attached to the catheter adapter and extend radially outward. Each wing inclues a distal edge 125 and a proximal edge 126. The distal edge is convex.

Introducer needle assembly 30 includes introducer needle 31 having a sharp distal tip 32 defined by a bevel and a proximal end connected to a needle hub 34. Introducer needle 31 is preferably formed from stainless steel and has a longitudinal axis that is generally parallel to the longitudinal axis of catheter and introducer needle assembly 30. Preferably, introducer needle 31 defines a notch, i.e., and opening in the sidewall of introducer needle 31. This allows blood to flow into the distal open end of introducer needle 31, through the notch and into the annular space between introducer needle 31 and catheter 21. The blood can then flow into extension tube 25 to allow the clinician to confirm successful venipuncture. This configuration allows the clinician easily to observe blood flashback along the distal portion of the catheter and introducer needle assembly.

Alternatively, needle hub 34 can include an integrated flashback chamber having an open proximal end. Needle hub 34 may be formed from the same types of materials that are used to form catheter adapter 24. Of course, other materials could be used to form needle hub 34. The needle hub includes concave finger grips 134 having a substantially oval shape. The proximal end of the needle hub is convex, thereby forming a thumb pad 135. An opening 136 is disposed at the thumb pad at its center.

Introducer needle assembly 30 also includes needle shield 40, which includes housing 41 defining an internal cavity therein with a proximal opening and a distal opening in communication with the internal cavity. This allows introducer needle 31 to extend longitudinally through housing 41. The lock that prevents unwanted proximal and distal movement of sharp distal tip 32 of introducer needle 31 out of the distal end of needle shield 40 once sharp distal tip 32 has been proximally withdrawn into needle shield 40 can take many forms. Such a lock does not comprise this invention. The details of such a lock are described in U.S. patent application Ser. No. 09/717,148 filed Nov. 21, 2000 (P-4203P1P1P1).

Figure 8:
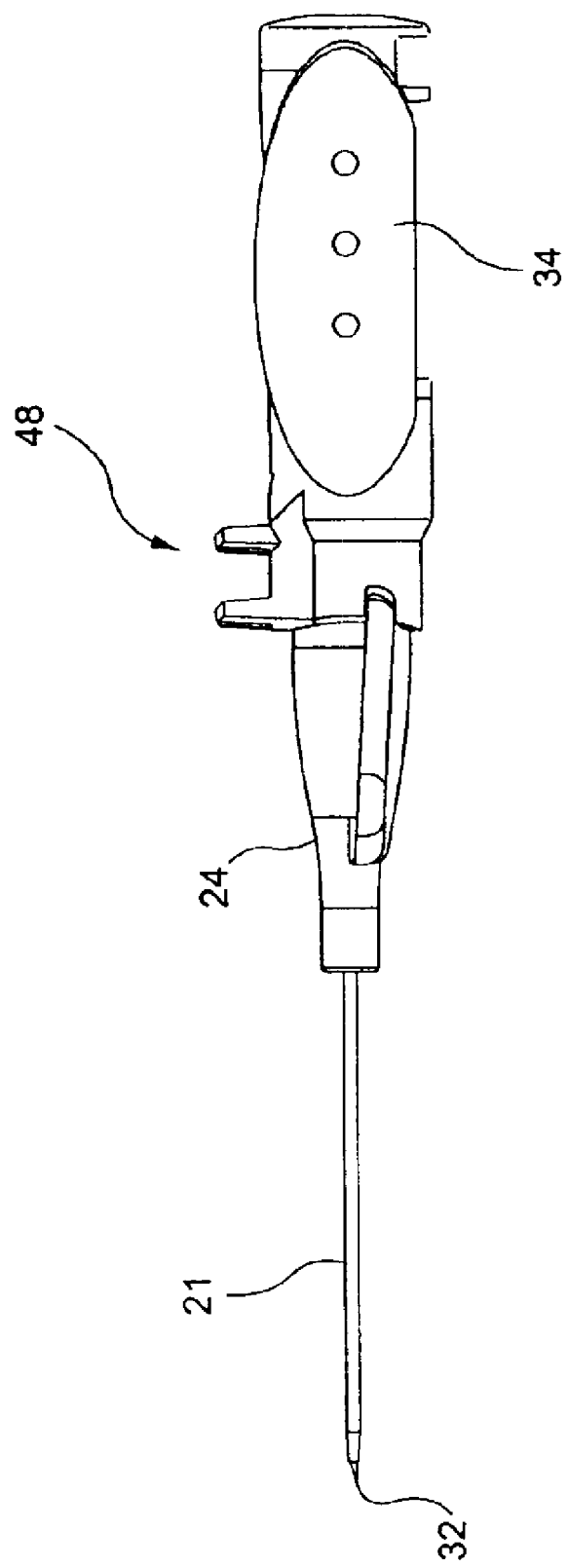
FIG. 8 is a side elevation view of a catheter with an introducer needle assembly including an alternate embodiment of the cantilever push tab of this invention ready for use.

A cantilever push tab 48 is associated with needle shield 40 and extends distally from the distal end of needle shield 40. Cantilever push tab 48 includes a cantilever portion 48a that extends distally from needle shield 40, preferably from an exterior surface of needle shield 40, and at least one upstanding tab portion 48b or "radially extending arm" at the distal end of cantilever portion 48a. If desired, multiple upstanding tab portions could be located at the distal end of cantilever portion 48a. See FIG. 8. However, preferably a single upstanding tab portion is used. The upstanding tab portion has a convex distal face 148 and a concave proximal face 149. Ribs 150 are disposed on the distal face.

Cantilever portion 48a causes upstanding tab portion 48b to extend over the proximal portion of catheter adapter 24 adjacent to the top portion of catheter adapter 24 in the middle thereof. Preferably cantilever portion 48a has a length that allows the clinician to easily and comfortably move upstanding tab portion 48b with her finger. Upstanding tab portion 48b should be wide enough to allow a substantial portion of the clinician's finger to engage it. For example, upstanding tab portion 48b should be between about 0.25 inches and about 0.40 inches wide. Upstanding tab portion 48b should be high enough to allow the clinician's finger pad, not the finger nail, engage it but should not be so high as to be obtrusive. For example, upstanding tab portion 48b should be between about 0.1 and about 0.3 inches tall. Finally, upstanding tab portion 48b should be curved such that it is concave with respect to the clinician using the device. This curvature enhances comfort and ease of use for the clinician and facilitates the ability of the clinician to use the device.

Figure 7:
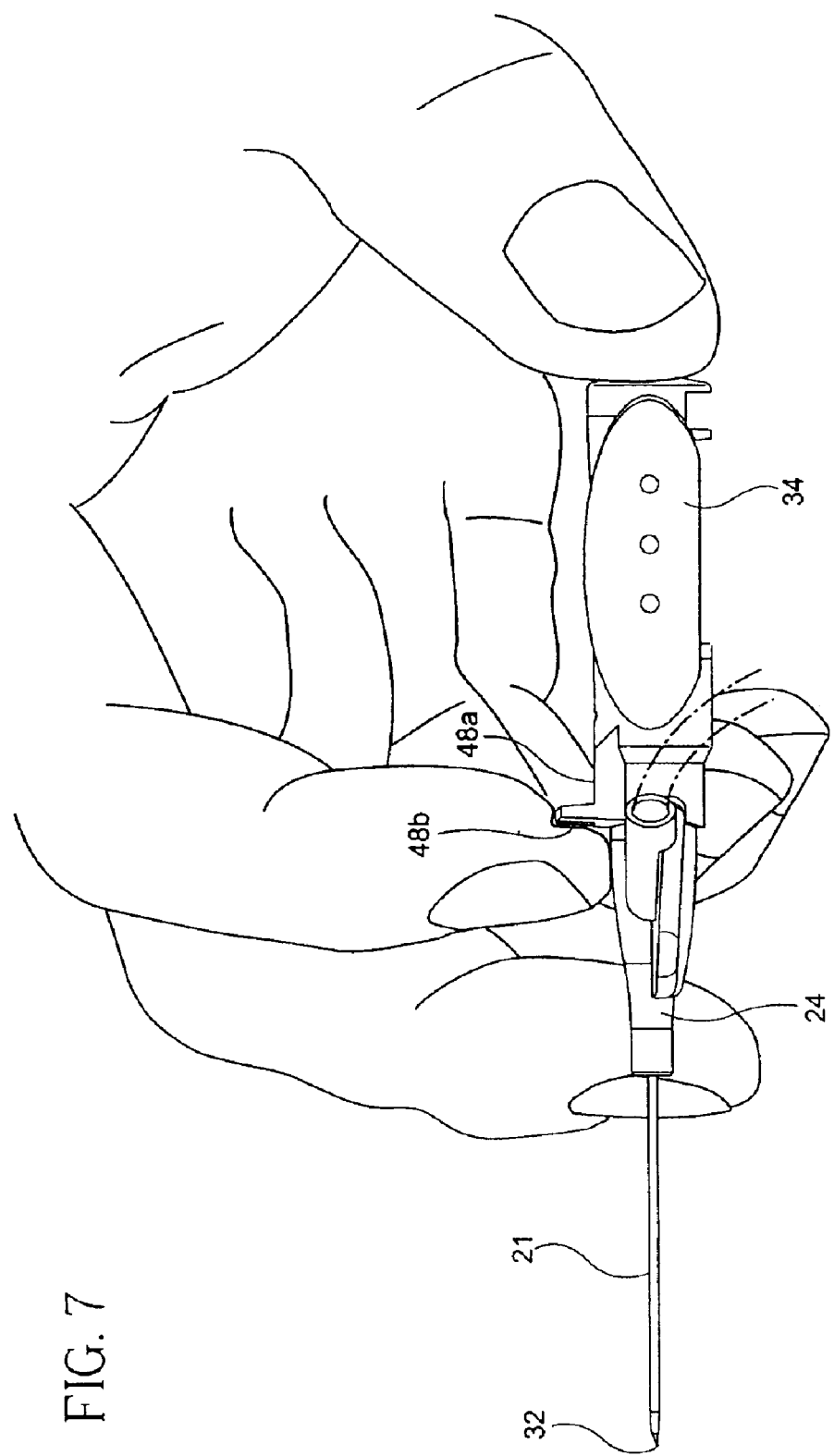
FIG. 7 is a side elevation view of a catheter with an introducer needle assembly including the cantilever push tab of this invention ready for use with the clinician's fingers shown in the position that may be used for inserting ported catheters.

Preferably upstanding tab portion 48b is located adjacent to where the sideport would be located in a typical ported catheter. This location allows a clinician to insert catheter 21 using a number of different techniques. Such techniques include, but are not limited to, a single handed technique that may be used for inserting ported catheters, a single handed technique that may be used for inserting a straight catheter, and a two handed technique. For example, upstanding tab portion 48b allows the clinician to grasp catheter and introducer needle assembly 10 by placing the thumb of one hand on the proximal end of needle hub 34 and the forefinger or middle finger of that same hand on the distal side of upstanding tab portion 48b. See FIG. 7. Once successful venipunture is achieved, the clinician may use the forefinger or middle finger of that hand to push against upstanding tab portion 48b to insert catheter 21 into a patient and advance needle shield 40 to cover sharp distal tip 32 of introducer needle 31. Alternatively, a clinician can use her other hand to push against upstanding tab portion 48b to push needle shield 40 and thus catheter assembly 20 distally away from needle hub 34. In addition, a clinician can disregard cantilever push tab 48 and insert catheter 21 using a single handed technique that is typically used for inserting a straight catheter. With this technique, the clinician typically grasps the assembly by placing the thumb and forefinger or middle finger of one hand on either side of needle hub 34. When successful venipuncture has occurred, the clinician uses the forefinger of that hand to push against upstanding tab portion 48b to advance needle shield 40 and thus catheter assembly 20 distally. The clinician can also use cantilever push tab 48 as a place holder for the clinician's forefinger when the clinician does not need to push against upstanding tab portion 48b.

In order to place catheter 21 into a patient's blood vessel, the clinician substantially longitudinally aligns introducer needle 31 and catheter 21 with the target blood vessel. The bevel of sharp distal tip 32 should be facing substantially away from the skin surface during venipuncture. The clinician inserts introducer needle 31 and catheter 21 at a shallow angle, preferably less than about 35 degrees, into the skin so that sharp distal tip 32 enters the target blood vessel. The clinician then preferably observes a blood flashback along integrated extension tube 25.

After confirming placement of introducer needle 31 and catheter 21 in the target blood vessel, the clinician advances catheter 21 distally axially along introducer needle 31 into position in the blood vessel by pushing against cantilever push tab 48. In certain techniques, introducer needle 31 may be partially withdrawn into catheter 21 before catheter 21 is completely advanced into position in the blood vessel. After proper placement of catheter 21 is achieved, the clinician places a finger from her other hand on the patient's skin over the blood vessel approximately over the distal end of catheter 21. By placing her finger on the patient's skin and applying sufficient pressure on the skin, the clinician thereby substantially occludes or at least minimizes blood flow through catheter 21. The clinician then places one finger against cantilever push tab 48 and simultaneously pulls on needle hub 34 in order to move needle hub 34 proximally and thus withdraw introducer needle 31 from catheter 21. As needle hub 34 is moved proximally with respect to catheter 21, the sharp distal tip enters into and is trapped in needle shield 40. Introducer needle 31 and needle shield 40 may then be disposed of according to the facility's disposal protocol Thus, it is seen that an introducer needle assembly is provided that allows a catheter to be inserted by a clinician using virtually any clinically acceptable technique and regardless of whether a ported catheter or a straight catheter is being inserted into a patient.

We claim:

1. A multi-grip needle and catheter assembly, comprising:
   an introducer needle having a proximal end and a distal end;
   a needle hub connected to the proximal end of the introducer needle, wherein the needle hub includes lateral sides, a proximal end and a distal end;
   concave finger grips, each having a substantially oval shape and disposed along the lateral sides of the needle hub;

wherein the proximal end of the needle hub has a convex shape, thereby forming a thumb pad;

a needle shield having an external surface, a distal end and a proximal end and being slidably disposed about the introducer needle distal of the needle hub, wherein at least the proximal end of the needle shield is disposed between the finger grips;

a push tab extending radially from the distal end of the needle shield having a convex distal face and a concave proximal face, wherein the push tab is distal to the finger grips;

a catheter having a proximal end and a distal end, wherein the catheter is slidably disposed about the introducer needle;

a catheter adapter connected to the proximal end of the catheter and having a proximal end and a distal end;

at least one wing attached to the catheter adapter and extending radially outward, wherein the wing includes a distal edge and a proximal edge, wherein the distal edge is convex and positioned distal to the push tab.

2. The needle and catheter assembly of claim 1 further comprising a side port attached to the catheter adapter and disposed proximal of the distal edge of the wing.

3. The needle and catheter assembly of claim 2 further comprising ribs disposed on the proximal face and the distal face of the push tab.

4. The needle and catheter assembly of claim 3 wherein an opening is disposed in the thumb pad at its center.

5. The needle and catheter assembly of claim 4 wherein the push tab is between 0.1 and 0.3 inches tall.

6. The needle and catheter assembly of claim 5 wherein the push tab comprises a cantilever portion extending distally from the needle shield and at least one upstanding tab portion at a distal end of the cantilever portion.

7. The needle and catheter assembly of claim 1 wherein the distal edge of the at least one wing is a smooth continuous surface and the proximal edge of the at least one wing is straight.

8. A multi-grip needle and catheter assembly, comprising:

an introducer needle having a proximal end and a distal end;

a needle hub connected to the proximal end of the introducer needle, wherein the needle hub includes lateral sides, a proximal end and a distal end;

finger grips disposed along the lateral sides of the needle hub;

a thumb pad disposed at the proximal end of the needle hub;

a needle shield having an external surface, a distal end and a proximal end and being slidably disposed about the introducer needle;

a push tab attached to and extending radially from the distal end of the needle shield, the push tab having a convex distal face and a concave proximal face, wherein the push tab is distal to the finger grips;

a catheter having a proximal end and a distal end, wherein the catheter is slidably disposed about the introducer needle;

a catheter adapter connected to the proximal end of the catheter and having a proximal end and a distal end;

a wing attached to the catheter adapter and extending radially outward, wherein the wing includes a distal edge and a proximal edge, wherein the distal edge is positioned distal to the push tab.

9. The multi-grip needle and catheter assembly of claim 8 wherein:

the finger grips have an oval shape;

the thumb pad is convex;

the needle shield is disposed between the finger grips;

the push tab is between 0.1 and 0.3 inches tall, and 0.40 inches wide; and the distal edge of the wing has a smooth, continuous convex shape along its entire length.

10. The multi-grip needle and catheter assembly of claim 9 further comprising a side port attached to the catheter adapter and formed integral with the wing.

11. A multi-grip needle and catheter assembly, comprising:

an introducer needle having a proximal end and a distal end;

a needle hub connected to the proximal end of the introducer needle, wherein the needle hub includes lateral sides, a proximal end and a distal end;

finger grips disposed along the lateral sides of the needle hub;

a thumb pad disposed at the proximal end of the needle hub;

a needle shield having an external surface, a distal end and a proximal end and being slidably disposed about the introducer needle;

a push tab attached to and extending radially from the distal end of the needle shield, wherein the push tab is distal to the finger grips;

a catheter having a proximal end and a distal end, wherein the catheter is slidably disposed about the introducer needle;

a catheter adapter connected to the proximal end of the catheter and having a proximal end and a distal end;

at least one wing attached to the catheter adapter and extending radially outward, wherein the wing includes a distal edge and a proximal edge, wherein the distal edge has a smooth convex shape and is positioned distal to the push tab.

12. The needle and catheter assembly of claim 11 further comprising a side port attached to the catheter adapter and disposed proximal of the distal edge of the wing.

13. The needle and catheter assembly of claim 11 further comprising ribs disposed on the proximal face and the distal face of the push tab.

14. The needle and catheter assembly of claim 11 wherein an opening is disposed in the thumb pad at its center.

15. The needle and catheter assembly of claim 11 wherein the push tab is between 0.1 and 0.3 inches tall.

16. The needle and catheter assembly of claim 11 wherein the push tab comprises a cantilever portion extending distally from the needle shield and at least one upstanding tab portion at a distal end of the cantilever portion.

17. The multi-grip needle and catheter assembly of claim 11 wherein:

the finger grips have an oval shape;

the thumb pad is convex;

the needle shield is disposed between the finger grips;

the push tab is between 0.1 and 0.3 inches tall, and 0.40 inches wide; and the proximal edge of the wing is straight.

* * * * *